United States Patent
Oh et al.

(10) Patent No.: US 10,675,316 B2
(45) Date of Patent: Jun. 9, 2020

(54) **COMPOSITION FOR PREVENTING AND TREATING CLIMACTERIC DISORDER CONTAINING EXTRACTS OF *DENDROPANAX MORBIFERA* LEV. AS ACTIVE INGREDIENT**

(71) Applicants: RIHU Healthcare Co., Ltd., Seoul (KR); AJOU UNIVERSITY INDUSTRY-ACADEMIC COOPERATION FOUNDATION, Suwon-si, Gyeonggi-do (KR)

(72) Inventors: Sung Moon Oh, Seoul (KR); Ga Hui Oh, Seoul (KR); Young-Joon Park, Seoul (KR); Minsun Chang, Seoul (KR)

(73) Assignees: RIHU HEALTHCARE CO., LTD., Seoul (KR); AJOU UNIVERSITY INDUSTRY-ACADEMIC COOPERATION FOUNDATION, Suwon-si, Gyeonggi-Do (KR)

( * ) Notice: Subject to any disclaimer, the term of this patent is extended or adjusted under 35 U.S.C. 154(b) by 138 days.

(21) Appl. No.: 16/066,986

(22) PCT Filed: Dec. 14, 2016

(86) PCT No.: PCT/KR2016/014652
§ 371 (c)(1),
(2) Date: Jun. 28, 2018

(87) PCT Pub. No.: WO2017/116045
PCT Pub. Date: Jul. 6, 2017

(65) Prior Publication Data
US 2018/0353559 A1 Dec. 13, 2018

(30) Foreign Application Priority Data
Dec. 30, 2015 (KR) .......................... 10-2015-0190242

(51) Int. Cl.
A61K 36/25 (2006.01)
A23L 33/105 (2016.01)
A61P 5/24 (2006.01)

(52) U.S. Cl.
CPC ............ *A61K 36/25* (2013.01); *A23L 33/105* (2016.08); *A61P 5/24* (2018.01)

(58) Field of Classification Search
CPC ..................................................... A61K 36/25
See application file for complete search history.

(56) References Cited

U.S. PATENT DOCUMENTS

2009/0042818 A1  2/2009 Cohen

FOREIGN PATENT DOCUMENTS

KR  2000-0004499 A   1/2000
KR  10-1485705 B1    1/2015
(Continued)

OTHER PUBLICATIONS

English language bibliographic information for DP Biotech Co. Ltd., KR 2003-075999 A, 2003.*

(Continued)

*Primary Examiner* — Rosanne Kosson
(74) *Attorney, Agent, or Firm* — Novick, Kim & Lee, PLLC; Jae Youn Kim

(57) ABSTRACT

Provided is a composition for preventing and treating a menopausal disorder containing extracts of *Dendropanax morbifera* LEV. as an active ingredient. Specifically, the extracts of *Dendropanax morbifera* LEV. exhibit a significant ER agonist activity within a cell, and exhibit a very potent ER agonist (full agonist) activity with an $EC_{50}$ value of about 100 μg/ml. Thus, the extracts of *Dendropanax morbifera* LEV. comprising a high content of plant metabolites similar to estrogen can be useful as hormone replacement therapy capable of improving various symptoms (Continued)

derived from a deficiency of estrogen in menopausal women.

8 Claims, 1 Drawing Sheet

(56) References Cited

FOREIGN PATENT DOCUMENTS

| KR | 10-2015-0037101 A | 4/2015 |
| WO | 2004-019676 A2 | 3/2004 |

OTHER PUBLICATIONS

*Dendropanax morbifera LEV.*, Good for Menstrual irregularity and Climacterium?!, Naver blog, Mar. 25, 2013, inner pp. 1-4, URL: http:// blog.naver.com/any778899/80186163173, pp. 1-4.

\* cited by examiner

COMPOSITION FOR PREVENTING AND TREATING CLIMACTERIC DISORDER CONTAINING EXTRACTS OF *DENDROPANAX MORBIFERA* LEV. AS ACTIVE INGREDIENT

TECHNICAL FIELD

The present invention relates to a pharmaceutical composition for preventing and treating a climacteric disorder containing extracts of *Dendropanax morbifera* LEV. as an active ingredient and a health food for preventing and improving the disorder.

BACKGROUND ART

Modern people who live in the modern society, industrialized by the advance of science and civilization, experience decreased immunity and aging with gradual extension of life span, due to various stresses, pollution and spontaneous aging, etc. In particular, women experience physical and mental difficulties due to climacteric symptoms that start gradually in their forties.

Climacteric refers to a transition period in which physiological and sexual functions are reduced or lost due to the reduction of the female hormone, estrogen, resulting from the overall and gradual aging of ovarian functions, which is an endocrine syndrome. Climacteric symptoms include: symptoms due to vascular changes, such as facial flushing, tachycardia, sweating or headache, symptoms due to musculoskeletal changes, such as myalgia, arthralgia and back pain, symptoms due to urogenital changes, such as urinary frequency and urinary incontinence, and symptoms due to changes in the brain-nervous systems, such as memory loss, depression, loss of concentration, and dizziness. Other symptoms include macular degeneration and changes in skin and hair. Further, the hormonal changes may cause fatal diseases for women's health such as osteoporosis, cardiovascular diseases, and the like.

Therefore, there has been a need to develop a therapeutic agent capable of improving climacteric symptoms in order to improve the physical and mental health and the quality of life of middle-aged women. In order to improve these climacteric symptoms, drugs such as hormone replacement therapy and non-steroidal drugs have been developed. However, most of the drugs are known to have side effects such as headache and weight gain. Especially, it is known that estrogen replacement therapy may increase the risk of metrorrhagia, stroke, heart attack, breast cancer and uterine cancer, along with adverse reactions thereto, since the hormone is artificially administered into the body (Swaran L., et. al., Obstetrics & Gynecology, 91, 678-684, 1998).

Due to these problems, there is a growing interest in replacing estrogen therapy with natural methods of taking a food or an additive. Also, there is a need to develop a new climacteric remedy that has an excellent effect of alleviating climacteric symptoms without side effects.

Estrogen has a variety of biological functions including increasing cell numbers and cell differentiation. Estrogen exert its biological actions through two estrogen receptors, estrogen receptor-alpha (ER-α) and estrogen receptor-beta (ER-β), which belong to the nuclear receptor superfamily (Nilsson et al., 2001, Physiol. Rev., 81(4):1535-1565.). The action mechanism of the estrogen receptors (ERs) is that estrogen binds to intracellular estrogen receptors to form receptor dimers, which then bind to specific estrogen response elements (EREs) located in the promoter of the target gene to regulate the expression of the target gene. The two estrogen receptors have different tissue distribution patterns and ligand binding forces from each other, and this difference allows them to selectively play different roles as an agonist or an antagonist in different tissues (Kuiper et al., 1997, Endocrinology, 138(3):863-870.). Materials acting on estrogen receptors have been used as targets for developing hormone replacement therapy for menopausal women and chemotherapeutic agents for genital cancer. Therefore, relevant researches have been continuously conducted to find out natural products that activate estrogen receptors without side effects on the human body, because they could be useful for treatment and prevention of climacteric disorders.

*Dendropanax morbifera* LEV. is an evergreen broad-leaved forest tree belonging to the Araliaceae. It is a native tree species of Korea naturally growing in Jeju Island and the southwest coast area such as Wando, Bogildo Island and Haenam in Korea. The clove ingredient contained in *Dendropanax morbifera* LEV. includes a small amount of terpenes and a large amount of sesquiterpenes. It contains germacrene-d, β-selinene, α-amorphene, α-selinene, δ-cadinene, γ-cadinene, T-muurolol, β-elemene, bicyclo[4,4,0]dec-1-en-2-isopropyl-5-methyl-9-methylene, β-cadinene, germacrene-B, α-copaene, α-humulene, and α-cadinene, a small amount of linalool L, α-terpinene, α-cubebene, α-ylangene, (+)-calarene, 3,7-guaiadine, (-)-isoledene, β-cubebene, limonene, aromadendrene, and cadina-1,4-diene, etc., although there is a difference depending on the time and place of collection (Jeollanam-do, 1996). Meanwhile, literature records show that *Dendropanax morbifera* LEV. is effective for alcohol detoxification, treatment of an eye disease and jaundice, burn treatment, leprosy and is harmless to the human body (Li Shizen, Ben Cao Gang Mu (Compendium of Materia Medica), Munkwang Books of China, 1590). Also, it is known to exhibit sedative and tonic actions (Research on Unique Agricultural and Marine Products to be Globalized, section of *Dendropanax morbifera* LEV., Jeollanam-do, 1996). It is also known that the leaf extract fraction thereof has anticancer activity and a slightly weaker antioxidative action than α-tocopherol (Korean Patent Laid-Open No. 2000-0004499, Ho-Keun Park et al., 1998). However, the effect of *Dendropanax morbifera* LEV. on climacteric is not known at all.

Therefore, the present inventors have made efforts to develop a therapeutic agent for treating a climacteric disorder derived from a natural product and which is safe for the human body. As a result, the present inventors have found that extracts of *Dendropanax morbifera* LEV. exhibit a significant ER agonist activity within a cell, and exhibit a very potent ER agonist (full agonist) activity with an $EC_{50}$ value of about 100 µg/ml. Thus, the present inventors have found that the extracts of *Dendropanax morbifera* LEV. comprising a high content of plant metabolites similar to estrogen can be useful as hormone replacement therapy capable of improving various symptoms derived from a deficiency of estrogen in menopausal women, and thereby completed the present invention.

SUMMARY OF INVENTION

Technical Problem

The object of the present invention is to provide a pharmaceutical composition for preventing and treating a climacteric disorder containing extracts of *Dendropanax*

*morbifera* LEV. as an active ingredient and a health food for preventing and improving the disorder.

Solution to Problem

In order to achieve the above object, the present invention provides a pharmaceutical composition for preventing and treating a climacteric disorder containing extracts of *Dendropanax morbifera* LEV. as an active ingredient.

In addition, the present invention provides a health food for preventing and improving a climacteric disorder containing extracts of *Dendropanax morbifera* LEV. as an active ingredient.

In addition, the present invention provides a method for preventing or improving a climacteric disorder comprising the step of administering to a subject a pharmaceutically effective amount of extracts of *Dendropanax morbifera* LEV.

In addition, the present invention provides a method for treating a climacteric disorder comprising the step of administering to a subject a pharmaceutically effective amount of extracts of *Dendropanax morbifera* LEV.

In addition, the present invention provides a use of extracts of *Dendropanax morbifera* LEV. for pharmaceutical compositions for preventing and treating a climacteric disorder.

In addition, the present invention provides a use of extracts of *Dendropanax morbifera* LEV. for health foods for preventing and improving a climacteric disorder.

Advantageous Effects of Invention

The extracts of *Dendropanax morbifera* LEV. of the present invention exhibit a significant ER agonist activity within a cell and in vivo, and exhibit a very potent ER agonist (full agonist) activity with an $EC_{50}$ value of about 100 μg/ml. Thus, the extracts of *Dendropanax morbifera* LEV. comprising a high content of plant metabolites similar to estrogen can be useful as hormone replacement therapy capable of improving various symptoms derived from a deficiency of estrogen in menopausal women.

DESCRIPTION OF EMBODIMENTS

Embodiments

Figure 1:
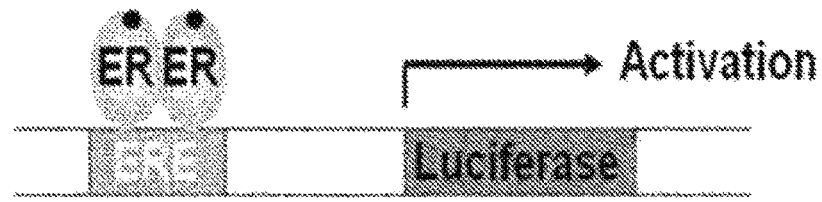
FIG. 1 is a diagram showing an outline of the ER-ERE luciferase assay.

Hereinafter, the present invention will be described in more detail.

The present invention provides a pharmaceutical composition for preventing and treating a climacteric disorder containing extracts of *Dendropanax morbifera* LEV. as an active ingredient.

It is preferable, but not limited thereto, that the extracts of *Dendropanax morbifera* LEV. as an active ingredient of the present invention be prepared by a method comprising the following steps:

1) adding an extraction solvent to at least one selected from the group consisting of leaves, stems, roots, and sap of *Dendropanax morbifera* LEV. to perform extraction;
2) filtering the extract obtained in step 1);
3) concentrating the filtrate obtained in step 2) under reduced pressure; and
4) drying the concentrate obtained in step 3).

In the preparation method of the present invention, cultivated or commercially available *Dendropanax morbifera* LEV. may be used without limitation as the *Dendropanax morbifera* LEV. of step 1).

In the preparation method of the present invention, the extraction solvent of step 1) is preferably water, an alcohol or a mixture thereof. The alcohol is preferably $C_1$ to $C_2$ lower alcohol, and the lower alcohol is preferably ethanol or methanol. The extraction method is preferably shaking extraction, Soxhelt extraction or reflux extraction, although not limited thereto. The amount of the extraction solvent for extraction is preferably 1 to 15 times, more preferably 2 to 10 times, the amount of the leaves, stems, or roots of washed and well-dried *Dendropanax morbifera* LEV. or of the collected sap of *Dendropanax morbifera* LEV. The extraction temperature is preferably 20° C. to 110° C., most preferably 30° C. to 105° C., although not limited thereto. In addition, the extraction time is preferably 1 to 72 hours, more preferably 2 to 48 hours, most preferably 2 to 5 hours, although not limited thereto. The number of times of extraction is preferably 1 to 5 times, more preferably 3 to 4 times, most preferably 3 times, although not limited thereto.

In the preparation method of the present invention, the concentration under reduced pressure in step 3) is preferably performed using a vacuum decompression concentrator or a vacuum rotary evaporator, although not limited thereto. The drying is preferably reduced-pressure drying, vacuum drying, boiling drying, spray drying or lyophilization, although not limited thereto.

When the material obtained from *Dendropanax morbifera* LEV. is sap, it is preferable to use water or lower alcohol to perform extraction, but it may also be used as a mixture with a powdered excipient.

The climacteric disorder refers to symptoms and disorders that occur in women during a perimenopausal period due to decreased estrogen secretion resulting from aging of the ovaries. Preferably, it refers to facial flushing, sweating, asteatosis, colpoxerosis, vaginal atrophy, atrophy of the lower urinary tract, vaginitis, cystitis, dysuria, urgency, concentration disorder, short-term memory impairment, anxiety, hypersensitivity, memory loss, myalgia, arthralgia or osteoporosis, although not limited thereto.

The composition exhibits an estrogen receptor agonist activity and thus has an effect of treating a climacteric disorder.

In a specific example of the present invention, extracts of *Dendropanax morbifera* LEV. were prepared, and then, in order to investigate the ER agonist activity or antagonist activity of extracts of *Dendropanax morbifera* LEV, a plasmid containing ERE-luciferase was transfected into cells, followed by treatment with the extracts of *Dendropanax morbifera* LEV. Then, the degree of luminescence of the products obtained by enzymatically decomposing luciferins was quantitatively measured using a luminometer. As a result, it was found that the extracts of *Dendropanax morbifera* LEV. of the present invention exhibited at least 50% of the efficacy of E2 at a powder concentration of 100 μg/ml, and 80% of the efficacy of E2 at a powder concentration of 200 μg/ml. Therefore, it was found that extracts of *Dendro-*

*panax morbifera* LEV. had an $EC_{50}$ value of about 100 μg/ml and were a very potent ER agonist (full agonist) (see Table 1).

In addition, as a result of testing the antagonist activity of extracts of *Dendropanax morbifera* LEV., it was found that extracts of *Dendropanax morbifera* LEV. did not affect the ER agonist activity of E2 at three test concentrations (50, 100, 200 μg/ml) (see Table 2).

In addition, extracts of *Dendropanax morbifera* LEV. alone or a combination of *Dendropanax morbifera* LEV. and E2 was subcutaneously injected to an animal model rat with a climacteric disorder which was ovariectomized to remove physiologically produced estrogen. As a result, it was found that the group administered with extracts of *Dendropanax morbifera* LEV. alone exhibited uterine proliferation as compared with the ovariectomized control group, and that the group administered with a combination of *Dendropanax morbifera* LEV. and E2 exhibited more uterine proliferation. Thus, it was found that extracts of *Dendropanax morbifera* LEV. had estrogen activity in vivo and did not affect the ER agonist activity of E2 (see Table 3 and FIG. 2).

Therefore, the extracts of *Dendropanax morbifera* LEV. of the present invention exhibit a significant ER agonist activity within a cell and in vivo, and exhibit a very potent ER agonist (full agonist) activity with an $EC_{50}$ value of about 100 μg/ml. Thus, the extracts of *Dendropanax morbifera* LEV. comprising a high content of plant metabolites similar to estrogen can be useful as an active ingredient of pharmaceutical compositions for preventing or treating various symptoms derived from a deficiency of estrogen in menopausal women.

The composition of the present invention may be administered orally or parenterally (for example, application or intravenous, subcutaneous, or intraperitoneal injection), but oral administration is preferred. Formulations for parenteral administration include external preparations, such as powders, granules, tablets, capsules, sterilized aqueous solutions, solutions, non-aqueous solutions, suspensions, emulsions, syrups, suppositories, and aerosols, and sterilized injections, which may be prepared by a conventional method. Preferably, the composition may be formulated into a pharmaceutical composition for external application to the skin, such as a cream, a gel, a patch, a spray, an ointment, an adhesive plaster, a lotion, a liniment, a paste or a cataplasma, although not limited thereto. The composition for topical administration may be anhydrous or water-based, depending on the clinical prescription. Propylene glycol, polyethylene glycol, vegetable oils such as olive oil, injectable esters such as ethyl oleate may be used for the non-aqueous solutions and suspensions. Examples of the matrix for the suppositories include witepsol, macrogol, tween 61, cacao butter, laurinum, glycerogelatin. Solid formulations for oral administration include powders, granules, tablets, capsules, soft capsules, and pills. Examples of liquid formulations for oral administration include suspensions, liquids for internal use, emulsions, syrups, and aerosols. They may include various excipients such as humectants, sweeteners, fragrances and preservatives, in addition to water and liquid paraffin, which are commonly used simple diluents.

In order to allow administration, the composition may comprise at least one pharmaceutically acceptable carrier in addition to extracts of *Dendropanax morbifera* LEV. The pharmaceutically acceptable carrier may be a saline solution, sterilized water, a Ringer's solution, a buffered saline solution, dextrose, maltodextrin, glycerol, ethanol or a mixture of one or more of these. If necessary, other conventional additives such as an antioxidant, a buffer, a bacteriostatic agent, etc. may be added. In addition, a diluent, a dispersant, a surfactant, a binder, and a lubricant may be additionally added to formulate the composition into an injectable formulation such as an aqueous solution, a suspension and an emulsion.

The content of the pharmaceutically acceptable additive according to the present invention is preferably 0.1 to 90 parts by weight based on the composition.

The preferred dose of the composition of the present invention varies depending on the degree of absorption of the active ingredient in the body, the age, gender and the degree of obesity of the patient, but can be appropriately selected by those skilled in the art. However, in order to achieve the desired effects, the daily dose of the composition for adults is 0.0001 to 100 mg/kg of body weight, preferably 0.001 to 100 mg/kg of body weight in case of oral formulations. It may be administered once a day or in several divided doses per day. The dose does not limit the scope of the present invention by any means.

The composition of the present invention may further contain at least one active ingredient which exhibits the same or similar function to extracts of *Dendropanax morbifera* LEV., in addition to the extracts.

In addition, the present invention provides a health food for preventing and improving a climacteric disorder containing extracts of *Dendropanax morbifera* LEV. as an active ingredient.

The extracts of *Dendropanax morbifera* LEV. of the present invention exhibit a significant ER agonist activity within a cell and in vivo, and exhibit a very potent ER agonist activity with an $EC_{50}$ value of about 100 μg/ml. Thus, the extracts of *Dendropanax morbifera* LEV. comprising a high content of plant metabolites similar to estrogen can be useful as an active ingredient of health foods for preventing or treating various symptoms derived from a deficiency of estrogen in menopausal women.

The present invention may also provide a food composition containing extracts of *Dendropanax morbifera* LEV. of the present invention in combination with a sitologically acceptable carrier.

When the extracts of *Dendropanax morbifera* LEV. of the present invention are used as a food or beverage additive, the extracts may be used as they are or in combination with other food or food additive, and they may be suitably used according to a conventional method. The amount of extracts of *Dendropanax morbifera* LEV. may suitably be determined according to the purpose of use (prevention, health or therapeutic treatment). In the case of long-term intake for the purpose of health and hygiene or for the purpose of controlling health conditions, the extracts of *Dendropanax morbifera* LEV. pose no problem in terms of safety. Thus, they can be taken for a long period of time. The type of the food is not particularly limited. Examples of the foods to which the material can be added include meats, sausages, bread, chocolate, candies, snacks, confectionery, pizzas, ramen, other noodles, gums, dairy products including ice creams, various soups, beverages, teas, drinks, alcoholic beverages and multi-vitamin preparations. When extracts of *Dendropanax morbifera* LEV. are formulated into a beverage, the beverage may additionally contain liquid ingredients such as, but not limited to, various flavoring agents or natural carbohydrates as in conventional beverages, in addition to extracts of *Dendropanax morbifera* LEV. Examples of the natural carbohydrates include monosaccharides such as glucose and fructose, disaccharides such as maltose and sucrose, polysaccharides such as general sugar such as dextrin and cyclodextrin, and sugar alcohols such as xylitol, sorbitol, and erythritol. The content of the natural carbohydrate is generally about 1 to 20 g, preferably about 5 to 12 g per 100 ml of the composition of the present invention. In addition, natural flavoring agents such as thaumatin and stevia extracts, for example, rebaudioside A, glycyrrhizin, etc., and synthetic flavoring agents such as saccharin, aspartame, etc., may be used as the flavoring agents.

In another aspect, the food composition of the present invention may contain various nutrients, vitamins, minerals (electrolytes), flavors such as synthetic flavors and natural flavors, coloring agents, enhancers (cheese, chocolate, etc.), pectic acid and its salts, organic acids, protective colloidal thickeners, pH regulators, stabilizers, antiseptics, glycerin, alcohols, and carbonators used for carbonated drinks, etc. The food composition of the present invention may also contain fruit flesh for preparation of fruit beverages and vegetable beverages. These ingredients may be used alone or as a mixture. In general, the content of these additives is 0.001 to 50 parts by weight based on the total weight of the composition.

In addition, the present invention provides a method for preventing or improving a climacteric disorder comprising the step of administering to a subject a pharmaceutically effective amount of extracts of *Dendropanax morbifera* LEV.

The extracts of *Dendropanax morbifera* LEV. are extracted preferably with water, $C_1$ to $C_2$ lower alcohol or a mixed solvent thereof, and the lower alcohol is preferably ethanol or methanol.

When the material obtained from *Dendropanax morbifera* LEV. is sap, it is preferable to use water or lower alcohol for extraction, but a mixture of the sap with a powdered excipient may also be used.

The climacteric disorder refers to symptoms and disorders that occur in women during a perimenopausal period due to decreased estrogen secretion resulting from aging of the ovaries. Preferably, it refers to facial flushing, sweating, asteatosis, colpoxerosis, vaginal atrophy, atrophy of the lower urinary tract, vaginitis, cystitis, dysuria, urgency, concentration disorder, short-term memory impairment, anxiety, hypersensitivity, memory loss, myalgia, arthralgia or osteoporosis, although not limited thereto.

The extracts of *Dendropanax morbifera* LEV. exhibit an estrogen receptor agonist activity and thus have an effect of treating a climacteric disorder.

The extracts of *Dendropanax morbifera* LEV. of the present invention exhibit a significant ER agonist activity within a cell and in vivo, and exhibit a very potent ER agonist (full agonist) activity with an $EC_{50}$ value of about 100 μg/ml. Thus, the extracts of *Dendropanax morbifera* LEV. comprising a high content of plant metabolites similar to estrogen can be useful for preventing or improving various symptoms derived from a deficiency of estrogen in menopausal women.

In addition, the present invention provides a method for treating a climacteric disorder comprising the step of administering to a subject a pharmaceutically effective amount of extracts of *Dendropanax morbifera* LEV.

The extracts of *Dendropanax morbifera* LEV. of the present invention exhibit a significant ER agonist activity within a cell and in vivo, and exhibit a very potent ER agonist (full agonist) activity with an $EC_{50}$ value of about 100 μg/ml. Thus, the extracts of *Dendropanax morbifera* LEV. comprising a high content of plant metabolites similar to estrogen can be useful for treating various symptoms derived from a deficiency of estrogen in menopausal women.

In addition, the present invention provides a use of extracts of *Dendropanax morbifera* LEV. for pharmaceutical compositions for preventing and treating a climacteric disorder.

The extracts of *Dendropanax morbifera* LEV. are extracted preferably with water, $C_1$ to $C_2$ lower alcohol or a mixed solvent thereof, and the lower alcohol is preferably ethanol or methanol.

When the material obtained from *Dendropanax morbifera* LEV. is sap, it is preferable to use water or lower alcohol for extraction, but a mixture of the sap with a powdered excipient may also be used.

The climacteric disorder refers to symptoms and disorders that occur in women during a perimenopausal period due to decreased estrogen secretion resulting from aging of the ovaries. Preferably, it refers to facial flushing, sweating, asteatosis, colpoxerosis, vaginal atrophy, atrophy of the lower urinary tract, vaginitis, cystitis, dysuria, urgency, concentration disorder, short-term memory impairment, anxiety, hypersensitivity, memory loss, myalgia, arthralgia or osteoporosis, although not limited thereto.

The extracts of *Dendropanax morbifera* LEV. exhibit an estrogen receptor agonist activity and thus have an effect of treating a climacteric disorder.

The extracts of *Dendropanax morbifera* LEV. of the present invention exhibit a significant ER agonist activity within a cell and in vivo, and exhibit a very potent ER agonist (full agonist) activity with an $EC_{50}$ value of about 100 μg/ml. Thus, the extracts of *Dendropanax morbifera* LEV. comprising a high content of plant metabolites similar to estrogen can be useful as an active ingredient of compositions for preventing and treating various symptoms derived from a deficiency of estrogen in menopausal women.

In addition, the present invention provides a use of extracts of *Dendropanax morbifera* LEV. for health foods for preventing and improving a climacteric disorder.

The extracts of *Dendropanax morbifera* LEV. of the present invention exhibit a significant ER agonist activity within a cell and in vivo, and exhibit a very potent ER agonist (full agonist) activity with an $EC_{50}$ value of about 100 μg/ml. Thus, the extracts of *Dendropanax morbifera* LEV. comprising a high content of plant metabolites similar to estrogen can be useful as an active ingredient of health foods for preventing and improving various symptoms derived from a deficiency of estrogen in menopausal women.

EXAMPLES

Hereinafter, the present invention will be described in detail with reference to Examples, Test Examples and Preparation Examples.

However, the following Examples, Test Examples and Preparation Examples are provided for illustrative purposes only, and the scope of the present invention is not limited thereto.

Example 1: Preparation of Extracts of *Dendropanax morbifera* LEV 1-1. Preparation of Hot Water Extracts Leaves, stems, and roots of *Dendropanax morbifera* LEV. were collected, washed, well dried and pulverized to rough powders. Then, 125 g thereof was accurately weighed and placed in an extraction tank. 875 g of purified water was added thereto, and then extraction was performed at 100° C. for 12 hours. The resultant extract was filtered through a 100-μm filter, transferred to a concentration tank, and concentrated under reduced pressure of 600 mmHg at 60° C. until a solid content of 25% was reached. The concentrate was lyophilized to obtain powdered extracts.

1-2. Preparation of a Mixture of Hot Water Extracts of *Dendropanax morbifera* LEV. and Maltodextrin Leaves, stems, and roots of *Dendropanax morbifera* LEV. were collected, washed, well dried and pulverized to rough powders. Then, 125 g thereof was accurately weighed and placed in an extraction tank. 875 g of purified water was added thereto, and then extraction was performed at 100° C. for 12 hours. The resultant extract was filtered through a 100-μm filter, transferred to a concentration tank, and concentrated under reduced pressure of 600 mmHg at 60° C. until a solid content of 25% was reached. Dried extracts of *Dendropanax morbifera* LEV were prepared so that they contain 50% of the resultant concentrate and 50% of maltodextrin.

1-3. Preparation of 30% Ethanol Extracts of *Dendropanax morbifera* LEV.

Leaves, stems, and roots of *Dendropanax morbifera* LEV. were collected, washed, well dried and pulverized to rough powders. Then, 125 g thereof was accurately weighed and placed in an extraction tank. 600 g of 30% ethanol aqueous solution was added thereto, and then extraction was performed at 50° C. for 6 hours. The above extraction procedure was repeated two more times. The resultant extract was filtered through a 100-μm filter, transferred to a concentration tank, and concentrated under reduced pressure of 600 mmHg at 60° C. until a solid content of 25% was reached. The concentrate was lyophilized to obtain powdered extracts.

1-4. Preparation of Hot Water Extracts of Sap of *Dendropanax morbifera* LEV.

Sap of *Dendropanax morbifera* LEV. was collected, and 100 g thereof was accurately weighed and placed in an extraction tank. 100 g of purified water was added thereto, and then extraction was performed at 20° C. for 4 hours. The resultant extract was filtered through a 100-μm filter, transferred to a concentration tank, and concentrated under reduced pressure of 600 mmHg at 60° C. until a solid content of 25% was reached. Dried extracts of *Dendropanax morbifera* LEV were prepared so that they contain 50% of the resultant concentrate and 50% of maltodextrin.

1-5. Preparation of a Mixture of Hot Water Extracts of Sap of *Dendropanax morbifera* LEV. and Maltodextrin Sap of *Dendropanax morbifera* LEV. was collected, and 100 g thereof was accurately weighed. Dried extracts of *Dendropanax morbifera* LEV were prepared so that they contain 50% of the resultant concentrate and 50% of maltodextrin.

In order to perform the following test, the extracts of *Dendropanax morbifera* LEV. obtained in the section 1-1 above were prepared into 100 mg/μl of stock solution using DMSO as a solvent. After adding DMSO, the sample was dissolved by vortexing and centrifuged at 13,000 rpm for 10 minutes to remove a trace of insoluble powders.

Example 2: Cell Culture

The estrogen receptor-positive breast cancer cell line MCF-7 purchased from the American Type Culture Collection (ATCC) was cultured in a RPMI 1680 medium containing a solution of non-essential amino acids, antibiotics/antimycotics, sodium pyruvate and 10% fetal bovine serum as the basic medium. The cells were subcultured once a week on average. The cells were cultured in a phenol-red free RPMI 1680 medium containing stripped serum, obtained by treating serum with dextran-charcoal three times, 48 to 60 hours (2 to 3 days) before cell seeding. This medium was used until completion of a luciferase assay. The medium was used to avoid the estrogenic properties of phenol-red itself and the interaction between estrogen receptors and the hormones and growth factors, etc. present in a large amount in serum.

Test Example 1: Investigation of the ER Agonist or Antagonist Activity of Extracts of *Dendropanax morbifera* LEV In order to investigate the ER agonist or antagonist activity of extracts of *Dendropanax morbifera* LEV., a plasmid containing ERE-luciferase was transfected into cells, followed by treatment with extracts of *Dendropanax morbifera* LEV. Then, the degree of luminescence of the products obtained by enzymatically decomposing luciferins was quantitatively measured using a luminometer to determine the degree of transcriptional activity (FIG. 1).

Specifically, the breast cancer cells cultured in Example 2 were inoculated into a 24-well plate one day before transfection ($10^5$ cells/well). Then, ERE-luciferase plasmid DNA (0.25 μg/well) was transfected into the breast cancer cells using a Lipofectamine 2000 Transfection Reagent (Invitrogen).

Then, E2 (17β-estradiol) (ER agonist, 1 nM) (Sigma) and ICI 182,780 (Tocris) (pure ER antagonist, 1 μM) were used as the positive control groups. Also, tests were performed on the extracts of *Dendropanax morbifera* LEV. of the present invention prepared in Example 1 at three concentrations of 50 μg/ml, 100 μg/ml and 200 μg/ml. The concentration conditions of 50, 100, and 200 μg/ml were determined based on the concentration points at which appropriate luciferase activity was obtained in preliminary experiments performed at 1 to 200 μg/ml. The final amount of DMSO did not exceed 0.2% of the volume of the medium, and it was validated from a separate test that the amount of DMSO had no influence on the final test results. In order to investigate the ER agonist activity, the extracts of *Dendropanax morbifera* LEV. of the present invention were applied alone, and in order to investigate the ER antagonist activity, 1 nM E2 and the extracts of *Dendropanax morbifera* LEV. of the present invention were administered at the same time. Meanwhile, cells were treated with extracts of *Dendropanax morbifera* LEV. and the control group, and further cultured for an average of 18 to 24 hours. Then, a luciferase assay was performed according to the following procedure: The medium was removed and the cells were washed with cold PBS twice. Lysates were extracted with 1× passive lysis buffer, and 50 μl of lysates were mixed with 50 μl of luciferase assay reagent (Promega, solution including luciferin as the substrate of luciferase and a buffer suitable for enzyme reaction). Then, the resulting luminescence intensity was measured using a SpectraMax M5e (Molecular Device).

1-1. Validation of ER-ERE Luciferase Activity Assay by Treatment with the Control Group Drug The luciferase activity (unitless) of the solvent DMSO used as the vehicle control group was 57.8 (2.0% of the value of 1 nM E2; the luciferase activity of 1 nM E2 was 2859 (100%)), and the luciferase activity of E2+ICI (1 μM) was 47.8 (1.7% of the value of 1 nM E2). Thus, it was found that the values of all the control groups of the present invention fell within the empirical experimental value range, and the luciferase activity of each drug was in accord with the characteristics of the drug.

1-2. Investigation of the ER Agonist Activity of Extracts of *Dendropanax morbifera* LEV.

The luciferase activity of extracts of *Dendropanax morbifera* LEV. was expressed as % based on the luciferase activity of 1 nM E2.

As shown in the following Table 1, it was found that the extracts of *Dendropanax morbifera* LEV. exhibited at least 50% of the efficacy of E2 at a powder concentration of 100 µg/ml, and 80% of the efficacy of E2 at a powder concentration of 200 µg/ml. Therefore, it was found that extracts of *Dendropanax morbifera* LEV. had an $EC_{50}$ value of about 100 µg/ml and were a very potent ER agonist (full agonist) (see Table 1).

TABLE 1

| Sample | % based on the maximum activity of E2 (single material treatment) |
|---|---|
| 50 µg/ml of extracts of *Dendropanax morbifera* LEV. | 33% |
| 100 µg/ml of extracts of *Dendropanax morbifera* LEV. | 56% |
| 200 µg/ml of extracts of *Dendropanax morbifera* LEV. | 80% |

1-3. Investigation of ER Antagonist Activity of Extracts of *Dendropanax morbifera* LEV.

Extracts of *Dendropanax morbifera* LEV. and 1 nM E2 were applied at the same time and then the resulting luciferase activity was recorded. The activity of the test group was expressed as % based on the luciferase activity of 1 nM E2, as in Test Example 1-1 above.

As shown in Table 2 below, it was found that extracts of *Dendropanax morbifera* LEV. did not affect the ER agonist activity of E2 at three test concentrations (50, 100, and 200 µg/ml) (see Table 2).

Thus, it was found that extracts of *Dendropanax morbifera* LEV. did not have an ER antagonist activity.

TABLE 2

| Sample | % based on the maximum activity of E2 (single material treatment) |
|---|---|
| DMSO | 3% |
| E2 | 100% |
| E2 + ICI | 2% |
| 100 µg/ml of E2 and extracts of *Dendropanax morbifera* LEV. | 116% |

Test Example 2: Estrogenic Activity of Extracts of *Dendropanax morbifera* LEV. in an Animal Model with a Climacteric Disorder 2-1. Construction of an Animal Model with a Climacteric Disorder In order to investigate the effect of extracts of *Dendropanax morbifera* LEV. on climacteric disorders, an animal model with a climacteric disorder, from which estrogen physiologically produced in vivo has been removed, was constructed.

Specifically, 8-week-old SD female rats (Orient Bio, Korea) were purchased and subjected to 12 hours of bright illumination and 12 hours of dark illumination per day for one week. Then, the rats were ovarietomized (OVX) by surgery to remove physiologically produced estrogen. Specifically, the rats were anesthetized with isoflurane, and the abdomen was excised under anesthesia to remove the ovaries. After ovariectomy, the analgesic ketoprofen (5 mg/kg) was administered. Three ovariectomized rats were put in each cage and subjected to two weeks of recovery and blood estrogen wash-out to construct animal model rats (OVX group) with a climacteric disorder. In addition, sham rats (sham group) were constructed by excising the abdomen and then sewing the incisions with the ovaries left intact. In order not to affect the test results, feed with limited phytoestrogen (Harlan 2020X Teklad Global Soy Protein-free Extruded Rodent Diet) was provided to the rats. In addition, the procedures related to the rats used in the tests were reviewed and approved by the Institutional Animal Care and Use Committee (Animal testing authorization number: SMWU-IACUC-1602-030).

2-2. Investigation of Estrogenic Activity of Extracts of *Dendropanax morbifera* LEV. in Rats with a Climacteric Disorder In order to investigate the estrogenic activity of extracts of *Dendropanax morbifera* LEV. in vivo, extracts of *Dendropanax morbifera* LEV. were administered to the rats with a climacteric disorder of Test Example 2-1 and then the degree of uterine proliferation was measured.

Specifically, the rats of Test Example 2-1 that went through recovery were divided into the following seven groups: Sham group administered with corn oil, OVX group administered with corn oil (OVX control group), OVX group administered with a high concentration of E2 (OVX E2(H) group), OVX group administered with a low concentration of extracts of *Dendropanax morbifera* LEV. (OVX DM250 group), OVX group administered with a high concentration of extracts of *Dendropanax morbifera* LEV. (OVX DM500 group), OVX group administered with a low concentration of E2 (OVX E2(L) group), OVX group administered with a low concentration of E2 and a high concentration of extracts of *Dendropanax morbifera* LEV. (OVX E2(L)+DM500 group). Each group included 6 to 7 rats. E2 was administered at high and low concentrations to reflect the low estrogen levels during a perimenopausal period. Also, a combination of E2 and extracts of *Dendropanax morbifera* LEV. was administered to investigate the presence of antagonist activity against the ER agonist activity of E2. After dividing the rats into 7 groups, subcutaneous injection was performed as follows for 3 days: 1 ml/kg of corn oil to sham group and OVX control group, 5 µg/kg of E2 dissolved in corn oil to OVX E2(H) group, 250 mg/kg of extracts of *Dendropanax morbifera* LEV. dissolved in PBS to OVX DM250 group, 500 mg/kg of extracts of *Dendropanax morbifera* LEV. dissolved in PBS to OVX DM500 group, 0.5 µg/kg of E2 dissolved in corn oil to OVX E2(L) group, and 0.5 µg/kg of E2 dissolved in corn oil and 500 mg/kg of extracts of *Dendropanax morbifera* LEV. dissolved in PBS to OVX E2(L)+DM500 group. At this time, the body weight of the rats was measured every day so that a predetermined amount of the ingredients could be administered. After 3 days of subcutaneous injection, the rats were fasted for 24 hours and euthanized in a $CO_2$ chamber. The abdomen of the euthanized rats was incised and the uterus was removed. The uterus weight was measured after removing the fat as much as possible. The degree of uterine proliferation was calculated by dividing the uterus weight (mg) by the body weight (kg).

TABLE 3

| Group | Uterus weight (mg)/body weight (kg) | SE |
| --- | --- | --- |
| Sham | 2.20 | 0.320 |
| OVX control group | 0.54 | 0.198 |
| OVX E2(H) | 1.22 | 0.319 |
| OVX DM250 | 0.99 | 0.392 |
| OVX DM500 | 1.13 | 0.357 |
| OVX E2(L) | 0.81 | 0.150 |
| OVX E2(L) + DM500 | 1.22 | 0.273 |

Figure 2:
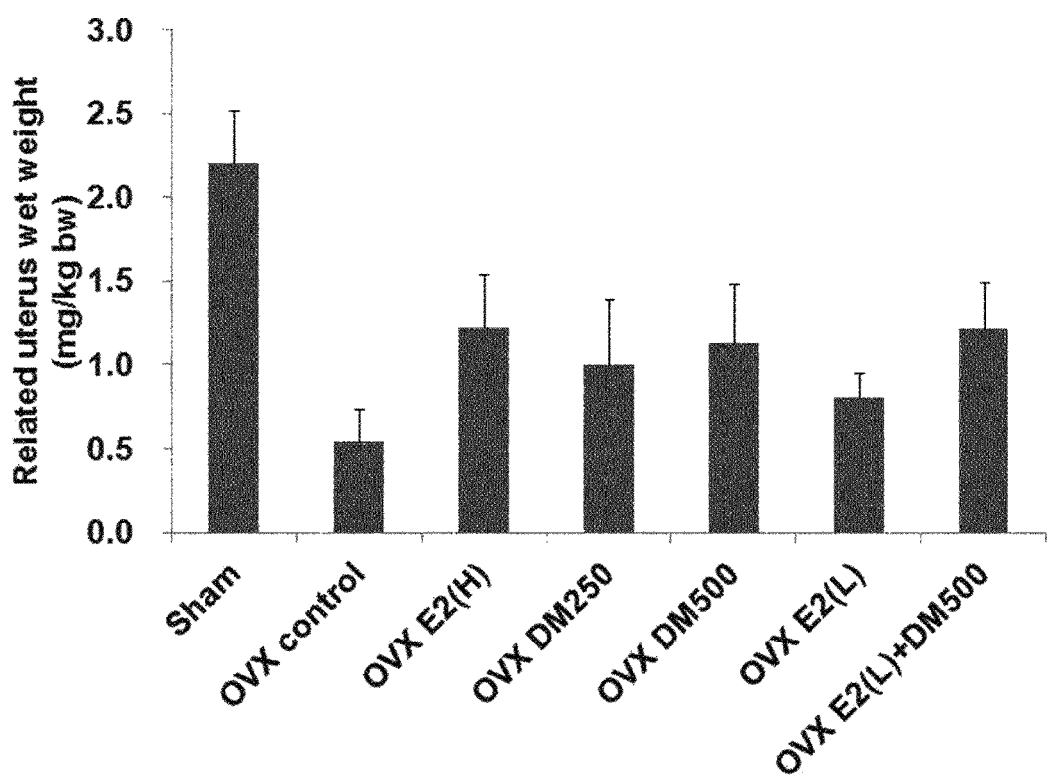
FIG. 2 is a graph showing the degree of uterine proliferation measured by administering extracts of *Dendropanax morbifera* LEV. or E2 to rats ovariectomized to remove estrogen and then extracting the uterus.

As a result, as shown in Table 3 and FIG. 2, it was found that OVX E2(H) group exhibited about 2.3 times more uterine proliferation than OVX control group and OVX DM250 group and OVX DM500 group respectively exhibited about 1.85 and 2.1 times more uterine proliferation than OVX control group. In addition, OVX E2(L)+DM500 group, administered with a combination of E2 and extracts of *Dendropanax morbifera* LEV., exhibited about 2.6 times more uterine proliferation than OVX control group. Thus, it was found that extracts of *Dendropanax morbifera* LEV. did not antagonize E2 and that they produced additional effects in addition to the E2-induced uterine proliferation (see FIG. 3 and Table 2).

The above results show that extracts of *Dendropanax morbifera* LEV. have an estrogenic activity in vivo and serve as an ER agonist together with E2. Thus, the extracts of *Dendropanax morbifera* LEV. can be used in female hormone replacement therapies for preventing and treating a climacteric disorder.

Preparation Example 1: Preparation of Pharmaceutical Preparations 1-1. Preparation of Powders
2 g of the extracts of *Dendropanax morbifera* LEV. of the present invention
  1 g of lactose
The above ingredients were mixed and filled in an airtight pouch to prepare powders.

1-2. Preparation of Tablets
100 mg of the extracts of *Dendropanax morbifera* LEV. of the present invention
  100 mg of microcrystalline cellulose
  100 mg of lactose
  18 mg of sodium starch glycolate
  2 mg of magnesium stearate
The above ingredients were mixed and subjected to a tableting process according to a conventional method for preparing tablets to prepare tablets.

1-3. Preparation of Capsules
100 mg of the extracts of *Dendropanax morbifera* LEV. of the present invention
  100 mg of corn starch
  100 mg of lactose
  2 mg of magnesium stearate
The above ingredients were mixed and filled in a gelatin capsule according to a conventional method for preparing capsules to prepare a capsule.

1-4. Preparation of Pills
1 g of the extracts of *Dendropanax morbifera* LEV. of the present invention
  1.5 g of lactose
  1 g of glycerin
  0.5 g of xylitol The above ingredients were mixed and prepared into pills according to a conventional method so that each pill contains 4 g of the ingredients.

1-5. Preparation of Granules
150 mg of the extracts of *Dendropanax morbifera* LEV. of the present invention
  50 mg of soybean extracts
  200 mg of glucose
  600 mg of starch
The above ingredients were mixed, added with 100 mg of 30% ethanol and dried at 60° C. to form granules, which were then filled in a pouch.

Preparation Example 2: Preparation of Foods 2-1. Preparation of Confectionery and Snacks
0.5 to 5.0 parts by weight of the extracts of *Dendropanax morbifera* LEV. of the present invention were added to wheat flour. The resultant mixture was prepared into bread, cakes, cookies, crackers and noodles to prepare foods for health promotion.

2-2. Preparation of Dairy Products
5 to 10 parts by weight of the extracts of *Dendropanax morbifera* LEV. of the present invention were added to milk, and then various dairy products such as butter and ice creams were prepared using the resultant milk.

2-3. Preparation of Sunsik
Brown rice, barley, glutinous rice, and *Coix lacryma-jobi* were gelatinized and dried according to a known method, followed by roasting. Then the resultant mixture was prepared into powders having a particle size of 60 mesh using a pulverizer. Black beans, black sesame seeds, and perilla seeds were steamed and dried according to a known method, followed by roasting. The resultant mixture was then prepared into powders having a particle size of 60 mesh using a pulverizer.

The extracts of *Dendropanax morbifera* LEV. of the present invention were concentrated under reduced pressure in a vacuum concentrator, sprayed and dried using a hot-air drier. The resultant was pulverized to a particle size of 60 mesh using a pulverizer to obtain dry powders. The above-prepared dry powders of grains, seeds and SBE were blended in the following ratio:

Grains (30 parts by weight of brown rice, 15 parts by weight of *Coix lacryma-jobi*, 20 parts by weight of barley)

Seeds (7 parts by weight of perilla seeds, 8 parts by weight of black beans, 7 parts by weight of black sesame seeds)

Dry powders of the extracts of *Dendropanax morbifera* LEV. of the present invention (3 parts by weight)

0.5 part by weight of *Ganoderma lucidum*, and 0.5 part by weight of Rehmannia *glutinosa*.

Preparation Example 3: Preparation of Beverages 1000 mg of the extracts of *Dendropanax morbifera* LEV. of the present invention
  1000 mg of citric acid
  100 g of oligosaccharide
  2 g of plum concentrate
  1 g of taurine
  Purified water to make a total of 900 ml
The above ingredients were mixed according to a conventional method for preparing health drinks, and heated with stirring at 85° C. for about 1 hour. The resultant solution was filtered and put in a sterilized 2-liter container, which was then sealed and sterilized, and stored in a refrigerator until it would be used for preparation of the health foods of the present invention.

The ingredients relatively appropriate for beverages were mixed according to the preferred mixing ratio, but the mixing ratio may be adjusted according to regional and national preferences, such as demand class, demand country, and purpose of use.

INDUSTRIAL APPLICABILITY

The present invention relates to a pharmaceutical composition for preventing and treating a climacteric disorder containing extracts of *Dendropanax morbifera* LEV. as an active ingredient and a health food for preventing and improving the disorder. The extracts of *Dendropanax morbifera* LEV. of the present invention can be useful as hormone replacement therapy capable of improving various symptoms derived from a deficiency of estrogen in menopausal women.

The invention claimed is:

1. A method for treating a climacteric disorder comprising the step of administering to a subject in need thereof a pharmaceutically effective amount of extracts of *Dendropanax morbifera* LEV. as an active ingredient.

2. The method for treating a climacteric disorder according to claim 1, wherein the extracts of *Dendropanax morbifera* LEV. are extracted with water, a C1 to C2 lower alcohol or a mixed solvent thereof.

3. The method for treating a climacteric disorder according to claim 1, wherein the lower alcohol is ethanol or methanol.

4. The method for treating a climacteric disorder according to claim 1, wherein the climacteric disorder is at least one selected from the group consisting of facial flushing, sweating, asteatosis, colpoxerosis, vaginal atrophy, atrophy of the lower urinary tract, vaginitis, cystitis, dysuria, urgency, concentration disorder, short-term memory impairment, anxiety, hypersensitivity, memory loss, myalgia and arthralgia.

5. The method for treating a climacteric disorder according to claim 1, wherein the extracts of *Dendropanax morbifera* LEV. are an estrogen receptor agonist.

6. A method for improving a climacteric disorder, comprising the step of administering to a subject in need thereof a pharmaceutically effective amount of extracts of *Dendropanax morbifera* LEV. as an active ingredient.

7. The method for improving a climacteric disorder according to claim 6, wherein the climacteric disorder is at least one selected from the group consisting of facial flushing, sweating, asteatosis, colpoxerosis, vaginal atrophy, atrophy of the lower urinary tract, vaginitis, cystitis, dysuria, urgency, concentration disorder, short-term memory impairment, anxiety, hypersensitivity, memory loss, myalgia, and arthralgia ad osteoporosis.

8. The method for improving a climacteric disorder according to claim 6, wherein the extracts of *Dendropanax morbifera* LEV. are an estrogen receptor agonist.

* * * * *